United States Patent [19]

Ono et al.

[11] Patent Number: 4,782,070
[45] Date of Patent: Nov. 1, 1988

[54] CEREBRAL DYSFUNCTION THERAPEUTIC AGENT, WHICH COMPRISES A DIHYDROPYRIDINE COMPOUND

[75] Inventors: Takaharu Ono, Osaka; Toshiharu Kamitani, Yamatokooriyama; Minoru Ohtsuka, Kobe, all of Japan

[73] Assignee: Fujisawa Pharmaceutical Co., Ltd., Osaka, Japan

[21] Appl. No.: 63,911

[22] Filed: Jun. 19, 1987

[30] Foreign Application Priority Data

Jul. 1, 1986 [JP] Japan ................... 61-154739

[51] Int. Cl.⁴ .............................. A61K 31/44
[52] U.S. Cl. ................................. 514/344
[58] Field of Search ......................... 514/344

[56] References Cited

PUBLICATIONS

Chem. Abst. 93-(1980), 220594G.

Primary Examiner—Stanley J. Friedman
Attorney, Agent, or Firm—Oblon, Fisher, Spivak, McClelland & Maier

[57] ABSTRACT

The treatment of cerebral dysfunction with a dihydropyridine compounds the formula:

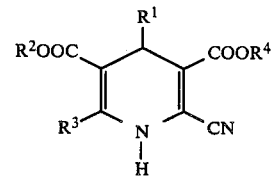

$R^1$ is nitrophenyl and $R^2$, $R^3$ and $R^4$ are each lower alkyl or a pharmaceutically acceptable salt thereof.

2 Claims, No Drawings

CEREBRAL DYSFUNCTION THERAPEUTIC AGENT, WHICH COMPRISES A DIHYDROPYRIDINE COMPOUND

This invention relates to a novel cerebral dysfunction therapeutic agent.

In detail, this invention relates to a novel cerebral dysfunction therapeutic agent, which comprises a dihydropyridine compound of the formula:

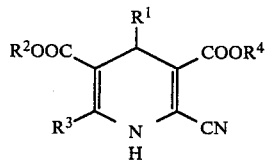

wherein
$R^1$ is nitrophenyl, and
$R^2$, $R^3$ and $R^4$ are each lower alkyl,
or a pharmaceutically acceptable salt thereof.

In more detail, this invention relates to a novel cerebral dysfunction therapeutic agent, which comprises, as an active ingredient, a dihydropyridine compound represented by the above formula (I) or a pharmaceutically acceptable salt thereof, which has improving activity of cerebral circulation and cerebral metabolism.

The dihydropyridine compound (I) used in this invention is known and has already been described in, for example, Japan Kokai No. 55-62065. Further, it is known that the dihydropyridine compound (I) has vasodilating activity and is useful for the treatment of ischemic heart diseases and hypertension.

A suitable pharmaceutically acceptable salt of the compound (I) is a conventional nontoxic salt and may include an acid addition salt such as an organic acid addition salt (e.g. formate, acetate, trifluoroacetate, maleate, tartrate, methanesulfonate, benzenesulfonate, toluenesulfonate, etc.); an inorganic acid addition salt (e.g. hydrochloride, hydrobromide, hydriodide, sulfate, nitrate, phosphate, etc.); a salt with an acidic amino acid (e.g. aspartic acid, glutamic acid, etc.); and the like.

It is known that some dihydropyridine derivatives (e.g. nicardipine, nimodipine, etc.) have improving activity of cerebral circulation.

However, with regard to nicardipine, duration of improving activity of cerebral circulation is short, and it is not known that it has improving activity of cerebral metabolism. And further, with regard to nimodipine, it is known that nimodipine improves electroencephalogram and brain ATP content after reperfusion, but not improve them during ischemia in the rat with transient cerebral ischemia, and also it has no effect on the liberation of free fatty acids in the same model. Accordingly, it was suggested that this improvement did not result from direct action on cerebral metabolism, but from the improvement of post-ischemic hyperfusion [Hideo Mabe et al., "Noshinkei", vol. 37, 1067 (1985)].

Under these circumstances, the development of a novel cerebral dysfunction thereapeutic agent, which has improving activity of metabolic disturbance due to cerebral ischemia in addition to more long-lasting and more potent activity of cerebral circulation, has been desired.

As a result of zealous study, the inventors of this invention have accomplished the invention by recognizing that dihydropyridine compound (I) or a pharmaceutically acceptable salt thereof has improving activity of cerebral circulation and further of cerebral metabolism, in addition to known vasodilating activity.

Accordingly, the object of this invention is to provide a novel cerebral dysfunction therapeutic agent, which comprises dihydropyridine compound (I) or a pharmaceutically acceptable salt thereof, in order to treat cerebrovascular diseases.

As such cerebrovascular diseases, there may be exemplified by cerebral infarction, cerebral hemorrhage, cerebral arteriosclerosis, and the like. The dihydropyridine compound (I) is useful not only for the treatment of these diseases, but also for the remission and/or treatment of many symptoms induced thereby (e.g. subjective symptom, psychotic symptom, neurological symptom, emotional disturbance, disturbance of cognition, etc.).

Suitable examples and illustrations of the various definitions of $R^1$, $R^2$, $R^3$ and $R^4$ used in the general formula of the dihydropyridine compound (I) are explained in detail as follows.

Suitable "nitrophenyl" for $R^1$ may include 2-nitrophenyl, 3-nitrophenyl and 4-nitrophenyl, in which more preferable example may be 3-nitrophenyl.

Suitable "lower alkyl" for $R^2$, $R^3$ and $R^4$ may include alkyl having 1 to 6 carbon atom(s) such as methyl, ethyl, propyl, isopropyl, butyl, isobutyl, sec-butyl, pentyl, isopentyl, neopentyl, 1- or 2-methylbutyl, hexyl, and the like, in which more preferable example may be $C_1$-$C_4$ alkyl, and the most preferable one may be isopropyl for $R^2$ and methyl for $R^3$ and $R^4$.

The cerebral dysfunction therapeutic agent used in the present invention can be administered orally or parenterally to a mammal including human being in a conventional pharmaceutical form such as capsules, micro-capsules, tablets, granules, powders, troches, pills, ointments, suppositories, injection solutions, syrups, and the like.

The cerebral dysfunction therapeutic agent of the present invention can be produced by the established procedures using various organic or inorganic carriers, which are conventional for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxymethyl cellulose, polypropylpyrrolidone, gelatin, gum arabic, polyethylene glycol, sucrose, starch, etc.), disintegrator (e.g. starch, carboxymethyl cellulose, hydroxypropyl starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent (e.g. hydroxypropylmethyl cellulose, etc.), diluting agent (e.g. water, etc.), base wax (e.g. cacao butter, white petrolatum, polyethylene glycol, etc.).

While the dosage of the active ingredient of the compound (I) is varied depending on various factors such as weight and/or age of patients and/or stages of the diseases, and further the kind of administration routes, it is administered in general by oral route at the daily dose level of 0.1 mg to 1000 mg, preferably 1 mg to 100 mg.

An effective single dose can be selected from the range of 0.001 mg/kg to 20 mg/kg, preferably 0.01 mg/kg to 2 mg/kg of the patients.

In order to show the usefulness of the dihydropyridine compound (I) or a pharmaceutically acceptable salt thereof used as an ingredient of the cerebral dysfunction therapeutic agent of this invention, the results of pharmacological tests are shown in the following.

Test 1: Effect on isolated canine basilar artery

Test Method

Under pentobarbital sodium anesthesia (35 mg/kg, ip or 30 mg/kg, iv), the basilar arteries (outside diameter: 1.0–1.5 mm) were isolated from mongrel dogs (weighing 8–18 kg) of either sex (6 dogs per group) and cut spirally (width 1 mm×length 15–20 mm). The spiral strips were suspended in a Tyrode's solution aerating with a gas mixture of 95% oxygen and 5% carbon dioxide, and the resting tension was adjusted to 0.5 g. After 1 hour, 35 mM potassium chloride was added to the organ bath to contract the arteries. The cumulative concentrations of the test compound, dissolved in a mixture of ethanol, polyethylene glycol and distilled water, were then added. Finally 0.1 mM papaverine was given to determine maximum relaxation. $ED_{50}$ Values (dose of the test compound which induces 50% relaxation) were calculated by interpolation from the dose-activity curves (effect of papaverine 0.1 mM=100%).

Test Compounds (1) Nicardipine (comparative compound)
(2) Isopropyl ester of 6-cyano-5-methoxycarbonyl-2-methyl-4-(3-nitrophenyl)-1,4-dihydropyridine-3-carboxylic acid (hereinafter referred to as Dihydropyridine Compound A)

Test Results (mean±standard error)

| Test Compounds | $ED_{50}$ ($\times 10^{-10}$M) |
| --- | --- |
| Nicardipine | 7.0 ± 0.7 |
| Dihydropyridine Compound A | 3.3 ± 0.4 |

Test 2: Effect on blood flow of the vertebral artery of dog

Test Method

Mongrel dogs of either sex (5–10 dogs per group), weighing 8–18 kg, were anesthetized with pentobarbital sodium (35 mg/kg, ip) and an electromagnetic flow-probe was fitted to the right vertebral artery and the blood flow of the vertebral artery was measured by a flow meter. Polyethylene cannulae were inserted into the femoral artery for measurement of blood pressure and into the femoral vein or the duodenum (after celiotomy) for administration of test compounds respectively.

Test compounds were dissolved in a mixture of ethanol, polyethylene glycol and distilled water, and administered in a volume of 0.2 ml/kg (iv) or 0.5 ml/kg (id). Incidentally, dogs were fasted for 18 hours in case of intraduodenum administration.

Test Compounds (1) Nicardipine
(2) Dihydropyridine Compound A

Test Results

| Maximum Changes of Blood Flow (%) | | | |
| --- | --- | --- | --- |
| | | Test Compounds | |
| Administration route | Dose (μg/kg) | Nicardipine | Dihydropyridine Compound A |
| iv | 3.2 | 31.4 ± 5.2 | 39.2 ± 7.2 |
| | 10 | 77.8 ± 17.4 | 86.4 ± 20.6 |
| | 32 | 91.7 ± 14.8 | 109.6 ± 18.3 |
| id | 10 | — | 17.2 ± 6.0 |
| | 32 | — | 39.7 ± 13.1 |
| | 100 | — | 89.3 ± 11.5 |
| | 320 | 33.7 ± 14.3 | — |
| | 1000 | 56.0 ± 28.5 | — |
| | 3200 | 131.3 ± 36.0 | — |

| Time-course of Changes of Blood Flow (%) (dose: 32 μg/kg, iv) | | |
| --- | --- | --- |
| | Test Compounds | |
| Time (minutes) | Nicardipine | Dihydropyridine Compound A |
| 5 | 91.7 ± 14.8 | 109.6 ± 18.3 |
| 10 | 73.4 ± 15.2 | 96.7 ± 16.2 |
| 20 | 48.1 ± 13.2 | 81.3 ± 15.5 |
| 30 | 37.0 ± 10.4 | 77.7 ± 12.5 |
| 60 | 23.0 ± 17.7 | 71.2 ± 17.5 |
| 90 | 8.2 ± 10.8 | 61.4 ± 25.7 |
| 120 | −0.5 ± 8.9 | 52.1 ± 23.1 |
| 180 | — | 31.0 ± 15.7 |

Test 3: Effect on blood flow in ischemic cerebral cortex of rat

Test Method

Male Wistar rats (5 rats per group), weighing 229–300 g, were anesthetized with thiopental sodium (50 mg/kg, ip). A skin incision was made in the middle of the right external auditory canal and the orbit, and a craniectomy (diameter: 2–2.5 mm) was made, using a dental drill, in the middle of the foramen ovale and the foramen opticum. After the dura was opened, the middle cerebral artery was exposed and occluded by electrocauterization using bipolar cautery.

After closure of the surgical wound, aminobenzylpenicillin (200 mg/kg) was divisionally administered into the operated part and subcutaneously.

One week after the surgery, the rats were anesthetized with urethane (1.25 g/kg, sc) and cannulae for artificial respiration and for measurement of blood pressure were inserted into the trachea and into the right femoral artery respectively, and then a stomach tube for administration of test compounds was inserted into stomach. The rats were fixed to stereotactic head-holders and craniectomies (diameter: 0.5 mm) were made on both sides of parietal skull, and then electrodes for measurement of local cerebral blood flow were inserted into right and left cerebral cortex (A=5, L=±5.0, H=2). For the measurement of blood flow, the rats were inhaled 100% hydrogen gas (5 ml/second, 5 seconds), and the cerebral blood flow was calculated from the clearance-curve recorded by tissue blood flow meter (made by Unique Medical Co., Ltd.).

The blood flows of the ischemic (occlusion side) and non-ischemic (non-occlusion side) cerebral cortex of the rats used in this test were 17.4±4.5 and 51.4±1.2 ml/brain 100 g/minute, respectively. Test Compounds were dissolved in 100% polyethylene glycol and administered orally in a volume of 1 ml/kg.

The blood flow was calculated according to the following calculating formula after obtaining a half life ($t_{\frac{1}{2}}$) from the clearance curve.

$$\text{Cerebral blood flow} = \lambda \frac{\log_e 2}{t_{\frac{1}{2}}} \times 100 \text{ (ml/100 g/minute)}$$

$\lambda$: partition coefficient of hydrogen gas between blood and tissues (=1.0)

$t_{\frac{1}{2}}$: a half life of concentration of hydrogen gas in brain

Test Compounds (1) Nicardipine
(2) Dihydropyridine Compound A

Test Results

| | Maximum Increase in Blood Flow (%) | | |
|---|---|---|---|
| | Dose (mg/kg) | Dihydropyridine Compound A | Nicardipine |
| Occlusion side | 0.1 | 12.6 ± 3.1 | 6.4 ± 1.3 |
| | 1.0 | 32.6 ± 4.6 | 15.9 ± 2.5 |
| Non-occlusion side | 0.1 | 13.6 ± 1.7 | 8.9 ± 3.2 |
| | 1.0 | 26.1 ± 4.8 | 20.5 ± 5.1 |

| Time-course of Vasodilation in Cortex of Occlusion Side (dose 1 mg/kg, po) | | | |
|---|---|---|---|
| | Increase in Blood Flow (%) | | |
| Time (minutes) | Vehicle | Dihydropyridine Compound A | Nicardipine |
| 15 | 2.7 ± 1.3 | 17.8 ± 2.4 | 6.2 ± 1.8 |
| 30 | 2.4 ± 1.4 | 27.4 ± 3.7 | 13.4 ± 2.8 |
| 45 | 4.1 ± 1.9 | 32.6 ± 4.6 | 15.9 ± 2.5 |
| 60 | 2.6 ± 1.4 | 28.3 ± 2.5 | 11.6 ± 2.9 |
| 90 | 0.6 ± 1.0 | 21.6 ± 6.4 | 8.8 ± 4.2 |
| 120 | 0.6 ± 0.8 | 17.5 ± 7.3 | 9.1 ± 5.3 |

Test 4: Remitting effect on a model of vasospasm after subarachnoid hemorrhage

Test Method

Mongrel cats of either sex (3–5 cats per group) were anesthetized with pentobarbital sodium (60 mg/kg, sc) and tracheal cannulae were inserted, and the test was carried out under spontaneous respiration. Following transcervical, transclival approach, the canine basilar artery was exposed by opening the dura and arachnoid maters, using an operating microscope. 30 Minutes after the surgery, a mixture of an equal volume of blood and cerebrospinal fluid (CSF) (0.2 ml) preincubated under an aseptic condition (37° C., 6–7 days) was applied on the surface of canine basilar artery. At the same time, the test compound [dissolved in a mixture of ethanol, polyethylene glycol and distilled water (2:1:7, v/v/v), administration volume: 0.2 ml] or only vehicle was administered into the right femoral vein. After 10 minutes, the blood-CSF mixture was carefully removed and microphotographs of the canine basilar artery were taken with the passage of time, and the inside diameter of the artery was measured from the microphotographs.

Test Compound

Dihydropyridine Compound A

Test Results

| | Time-course of Changes of the Diameter of the Artery (%) | | |
|---|---|---|---|
| | Dose (µg/kg) | | |
| Time (minutes) | 0 (only vehicle) | 10 | 100 |
| 15 | −29.4 ± 4.2 | 17.0 ± 4.5 | 16.6 ± 7.6 |
| 30 | −29.5 ± 5.9 | 17.1 ± 4.6 | 15.1 ± 5.1 |
| 45 | −23.8 ± 6.5 | 18.3 ± 5.3 | 25.9 ± 7.5 |
| 60 | −14.2 ± 5.0 | 17.8 ± 3.8 | 24.4 ± 7.5 |
| 90 | −9.3 ± 5.0 | 15.5 ± 3.2 | 21.6 ± 7.3 |
| 120 | −3.5 ± 3.9 | 17.1 ± 5.1 | 25.5 ± 7.9 |

Test 5: Effect on energy metabolism in ischemic brain

Test Method

Rats with unilateral middle cerebral artery occlusion (5–10 rats per group) were prepared in substantially the same manner as that of Test 3. Test compounds (1.0 mg/kg) (dissolved in polyethylene glycol, administration volume: 1 ml/kg) or vehicle was administered sc once a day for 3 days beginning from the fifth day after the surgery. One hour after the last administration, the rats were frozen in liquid nitrogen and then the whole brains of the both side excluding the cerebellum were isolated separately. The right hemisphere was homogenized with ice-cooled 6% perchloric acid (20 times in volume), centrifuged (3000 r.p.m., 10 minutes at 4° C.) and then the supernatant was neutralized with 5M potassium carbonate.

After the neutralization, the supernatant was centrifuged again and the concentrations of adenosine triphosphate (ATP) and lactic acid included in the resulting supernatant were measured by enzymatic assay.

Test Compounds (1) Nicardipine
(2) Dihydropyridine Compound A

Test Results

| | Effect on Energy Metabolism | | |
|---|---|---|---|
| | | ATP (µmol/ brain 1 g) | Lactic acid (µmol/ brain 1 g) |
| Occluded rat | Vehicle | 1.97 ± 0.06 | 3.84 ± 0.28 |
| | Nicardipine | 1.92 ± 0.11 | 3.84 ± 0.14 |
| | Dihydropyridine Compound A | 2.48 ± 0.07 | 2.89 ± 0.14 |
| | Normal rat | 2.38 ± 0.13 | 1.83 ± 0.18 |

Test 6: Effect on free fatty acid liberation due to decapitation ischemia

Test Method

Ten-week old male Wistar rats (6–9 rats per group) were used. After decapitation, the heads were incubated in saline at 37° C. for 10 minutes and then immediately frozen in liquid nitrogen. The isolated cerebrums were homogenized with a mixture of chloroform and methanol (2:1 v/v, 20 times in volume, containing myristic acid as an internal standard).

After centrifugation (3000 r.p.m., 10 minutes), 1 ml of the supernatant was dried in a stream of nitrogen and to the resulting residue was added a solution of diazomethane in diethyl ether (0.5 ml). The solution was allowed to stand at room temperature for 1 hour and then dried in a stream of nitrogen.

To a solution of the residue in a mixture of n-hexane and diethyl ether (20:1 v/v, 4 ml) was added silicic acid (200 mg), and the solution was shaked for 5 minutes and centrifuged (3000 r.p.m., 5 minutes). After 3 ml of the supernatant was dried in a stream of nitrogen, the resulting residue was dissolved in a mixture of n-hexane and diethyl ether (20:1 v/v, 100 μl) and 2 μl of the solution was used for gas chromatographic analysis. Each concentration of free fatty acids liberated was calculated by internal standard method (peak area). Ten minutes before decapitation, the test compound (dissolved in 100% polyethylene glycol, 100 μg/kg) or the vehicle was administered iv.

Test Compound

Dihydropyridine Compound A

Test Results

|  |  | Concentration of Liberated Free Fatty Acids (nmol/brain 1 g) | | | |
| --- | --- | --- | --- | --- | --- |
|  |  | Palmitic acid | Oleic acid | Arachidonic acid | Docosahexaenoic acid |
| Decapitation ischemia | Vehicle | 259 ± 14 | 166 ± 6 | 375 ± 8 | 83 ± 6 |
|  | Dihydropyridine Compound A | 219 ± 11 | 149 ± 4 | 335 ± 9 | 62 ± 4 |
| Normal brain |  | 76 ± 10 | 43 ± 7 | 0 | 6 ± 6 |

Test 7: Effect on Production of Lipid Peroxide in cerebral mitochondria of rat

Test Method

Cerebral mitochondria of male Wistar rats were isolated and mixed with a mixture of ascorbic acid (100 μM), ferrous sulfate (10 μM), ferric sulfate (20 μM) and test compound, and the mixture was incubated at 37° C. for 1 hour. The amount of malondialdehyde produced in the incubated mixture was measured by thiobarbituric acid method [Shimada et al., Biochim. Biophy. Acta, vol. 489, pp 163–172 (1977)].

Test Compound

Dihydropyridine Compound A

Test Results

| Inhibition of Production of Lipid Peroxide | |
| --- | --- |
| Concentration of Test Compound | Inhibition (%) |
| $2.6 \times 10^{-5}$ (M) | 96.94 ± 1.03 |
| $2.6 \times 10^{-4}$ (M) | 100.0 |

The abbreviations used in these tests were as follows.
ip: intraperitoneally
iv: intravenously
sc: subcutaneously
id: intraduodenumly
po: perorally The present invention is explained according to the following Examples.

EXAMPLE 1

| Dihydropyridine Compound A | 100 g |
| --- | --- |
| Hydroxypropylmethyl Cellulose | 500 g |

Dihydropyridine Compound A was dissolved in anhydrous ethanol (5 liters) and then hydroxypropylmethyl cellulose was added thereto to prepare a suspension. Then the organic solvent was removed under reduced pressure to give solid dispersion composition.

EXAMPLE 2

| Dihydropyridine Compound A | 100 g |
| --- | --- |
| Hydroxypropylmethyl Cellulose | 500 g |
| Sucrose | 9.4 kg |

To a suspension of Dihydropyridine Compound A and hydroxypropylmethyl cellulose in anhydrous ethanol (5 liters) was added sucrose and the resultant mixture was stirred. Then the organic solvent was removed under reduced pressure to give solid dispersion composition. This composition was converted into fine granules by a conventional method.

EXAMPLE 3

| Dihydropyridine Compound A | 100 g |
| --- | --- |
| Hydroxypropylmethyl Cellulose | 500 g |
| Lactose | 6.87 kg |
| Low-substituted Hydroxypropyl-Cellulose | 1.5 kg |
| Magnesium Stearate | 30 g |

To a suspension of Dihydropyridine Compound A and hydroxypropylmethyl cellulose in anhydrous ethanol (5 liters) were added lactose and low-substituted hydroxypropyl cellulose, and the resultant mixture was stirred and then the organic solvent was removed under reduced pressure to give solid dispersion composition. After this composition was converted into granules by a conventional method, the granules were further converted with magnesium stearate into tablets by a conventional method, each of which contains 2 mg of Dihydropyridine Compound A.

EXAMPLE 4

For each tablet obtained in Example 3, the coating layer consisting of hydroxypropylmethyl cellulose (5.1 mg), titanium dioxide (1.6 mg), polyethylene glycol-6000 (0.8 mg), talc (0.4 mg) and iron oxide yellow (0.1 mg) was film-coated by a conventional method to give a film-coated tablet containing 2 mg of Dihydropyridine Compound A.

What is claimed is:
1. A method for the treatment of cerebral dysfunction in a mammalian subject which comprises administering to said subject an effective amount of a dihydropryidine compound of the formula:

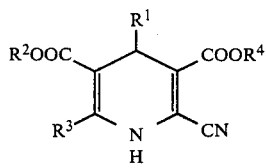
(I)

wherein
R¹ is 3-nitrophenyl, and
R², R³ and R⁴ are each lower alkyl,
or a pharmaceutically acceptable salt thereof.

2. A method according to claim 1, wherein the dihydropyridine compound is isopropyl ester of 6-cyano-5-methoxycarbonyl-2-methyl-4-(3-nitrophenyl)-1,4-dihydropyridine-3-carboxylic acid.

* * * * *